United States Patent
Chen et al.

(10) Patent No.: US 6,470,210 B1
(45) Date of Patent: Oct. 22, 2002

(54) SYSTEM AND METHOD FOR CONTINUOUSLY MONITORING CLASSIFIED ATRIAL ARRHYTHMIAS

(75) Inventors: Victor Chen, Minnetrista; Gary Seim, Minneapolis; Carlos Ricci, Apple Valley; LeAnne Eberle, St. Louis Park; Hal Propp, Oakdale; Clayton Foster, Andover, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/827,770

(22) Filed: Apr. 6, 2001

(51) Int. Cl.[7] .............................................. A61B 5/046
(52) U.S. Cl. ...................................................... 600/515
(58) Field of Search ................................. 600/518, 519, 600/509; 607/5

(56) References Cited

U.S. PATENT DOCUMENTS 5,868,793 A * 2/1999 Nitzsche et al.
6,253,102 B1 * 6/2001 Hsu et al.

* cited by examiner

Primary Examiner—Scott M. Getzow
(74) Attorney, Agent, or Firm—Crawford Maunu PLLC (57) ABSTRACT

Systems and methods are provided for analyzing occurrences of atrial arrhythmias. Occurrences of each of a number of classified atrial arrhythmia rhythms are detected. The classified atrial arrhythmias may, for example, include at least atrial fibrillation and atrial flutter. A duration of time associated with each of the detected atrial arrhythmia rhythms is measured. Trend data is produced with respect to a predetermined period of time using all or selected ones of the measured time durations. The detecting, measuring, and producing processes may also be performed for one or more unclassified atrial arrhythmias.

34 Claims, 9 Drawing Sheets

| AA Type | Start Date | Start Time | End Time | End Date | Duration | Count |
|---------|------------|------------|----------|----------|----------|-------|
| SVT$_2$ | 02/02/01 | 10:24 am | 12:48 pm | 02/02/01 | 2h, 24m | 11 |
| SVT$_2$ | 02/03/01 | 4:50 pm | 4:58 pm | 02/03/01 | 0h, 08m | 12 |
| SVT$_1$ | 02/04/01 | 5:02 am | 9:54 am | 02/04/01 | 4h, 52m | 5 |
| SVT$_1$ | 02/04/01 | 11:21 pm | 3:34 pm | 02/05/01 | 16h, 13m | 6 |
| SVT$_2$ | 02/06/01 | 2:05 pm | 7:37 pm | 02/06/01 | 4h, 32m | 13 |
| SVT$_1$ | 02/08/01 | 9:26 pm | 10:38 pm | 02/08/01 | 1h, 12m | 7 |
| AF | 02/11/01 | 1:03 pm | 2:14 pm | 02/11/01 | 1h, 11m | 1 |

Fig. 8

Diagnostic Output Data

Cumulative Elapsed Time of Each AA
Duration of Each AA Events
Time Between AA Events
Frequency of AA Events
Number, Frequency, Duration of AntiTachy Pacing or other Atrial Therapy
Number, Frequency, Duration of Defibrillation Therapy
Percentage Time of AA Events
Trends of Percentage Time of AA Events
Trends of Percentage Time of Cumulative AA Event Times
Trends of Events following ATP or Defibrillation Therapy
Other Data

SYSTEM AND METHOD FOR CONTINUOUSLY MONITORING CLASSIFIED ATRIAL ARRHYTHMIAS

FIELD OF THE INVENTION

The present invention relates generally to implantable medical devices and, more particularly, to implantable pacemakers and cardioverter-defibrillators for continuously monitoring and accurately measuring atrial arrhythmias.

BACKGROUND OF THE INVENTION

Implantable cardioverter-defibrillators (ICDs) have been developed that employ detection algorithms capable of recognizing and treating ventricular tachycardias and ventricular fibrillation. Detection algorithms are also being developed to recognize and treat atrial tachycardias and atrial fibrillation. In general, ICDs are designed to treat such tachycardias with antitachycardia pacing and low-energy cardioversion shocks in conjunction with back-up defibrillation therapy. These ICDs monitor the heart rate and the onset of the arrhythmia by sensing endocardial signals and determining when the heart is in need of either cardioversion to treat a given tachycardia or of defibrillation to treat a fibrillation condition.

Certain ICDs have been designed with dual chamber sensing capabilities to detect and analyze both ventricular and atrial endocardial signals. This increase in cardiac signal input to the ICD has provided an opportunity to determine the origin and the nature of atrial and ventricular tachyarrhythmia, and to reduce the frequency of inappropriate therapy being delivered to an implant patient.

However, while the combination of antitachycardia pacing with low and high energy shock delivery, as well as backup bradycardia pacing, in ICDs has expanded the number of clinical situations in which the device may appropriately be employed, improved means of continuously monitoring and accurately measuring atrial and/or ventricular arrhythmia burden is still desired.

For the reasons stated above, and for other reasons stated below which will become apparent to those skilled in the art upon reading the present specification, there is a need in the art for improved atrial and ventricular monitoring techniques. There exists a further need for such techniques that provide for increased monitoring specificity with respect to various types of atrial and ventricular arrhythmias. The present invention fulfills these and other needs, and provides several advantages over prior monitoring systems and techniques.

SUMMARY OF THE INVENTION

The present invention is generally directed to systems and methods for analyzing occurrences of atrial arrhythmias. According to an embodiment of the present invention, occurrences of each of a number of classified atrial arrhythmia rhythms are detected. The classified atrial arrhythmias may, for example, include at least atrial fibrillation and atrial flutter. A duration of time associated with each of the detected atrial arrhythmia rhythms is measured. Trend data is produced with respect to a predetermined period of time using all or selected ones of the measured time durations. The detecting, measuring, and producing processes may also be performed for one or more unclassified atrial arrhythmias.

Trend data may be produced from measured time duration data which has been stored or processed according to a desired format or formats. For example, atrial arrhythmia data may be formatted according to a log format or a time bin format.

Producing the trend data may include summing each of the time durations to produce a cumulative time duration associated with each of the classified atrial arrhythmia rhythms over the predetermined time period. Producing the trend data may also include computing changes in the respective cumulative time durations as a function of time over the predetermined time period.

According to one approach, a percentage of the predetermined time period during which each of the classified atrial arrhythmia rhythms was detected is computed using each of the time durations. Changes in the respective percentages may further be computed as a function of time over the predetermined time period.

The duration or percentage of time a given rhythm was detected during a given atrial arrhythmic episode or series of episodes may be computed using trend data analysis. The duration or percentage of time a given rhythm was detected over the course of a selected snapshot of time can also be computed. Various other types of histogram data may be developed to enhance analyses of atrial arrhythmias experienced by a patient.

In general, the predetermined time period is a selectively programmable period of time or a preestablished time period. For example, the predetermined time period may be selected as a 24 hour time period, a time period based on months or a time period based on years. The predetermined time period may further define a time period between patient analyses, which are typically conducted at a physician's office or a clinic. The predetermined time period may also represent a time period defined by a life time of a patient. The predetermined time period can also represent a time period defined by a life time of one or more implantable medical devices.

In accordance with another embodiment of the present invention, analyzing occurrences of classified atrial arrhythmias involves detecting occurrences of classified atrial fibrillation (AF) rhythms and detecting occurrences of classified supraventricular tachycardia (SVT) rhythms other than atrial fibrillation rhythms. The classified SVT rhythms may, for example, include atrial flutter rhythms. A duration of time (AF time duration) associated with each of the detected atrial fibrillation rhythms is measured. A duration of time (SVT time duration) associated with each of the detected SVT rhythms is also measured. Trend data is produced with respect to a predetermined period of time using the measured AF and SVT time durations.

Producing the trend data may involve summing the AF time durations to produce a cumulative AF time duration and summing the SVT time durations to produce a cumulative SVT time duration for the predetermined time period. Producing the trend data may further involve computing changes in the cumulative AF time duration as a function of time and computing changes in the cumulative SVT time duration as a function of time over the predetermined time period.

Additional trend data may be produced, such as by computing, using the AF time durations and the SVT time durations, a percentage (AF percentage) of the predetermined time period during which the classified AF rhythms were detected and a percentage (SVT percentage) of the predetermined time period during which the classified SVT rhythms were detected. Changes in the AF and SVT percentages may further be computed as a function of time over the predetermined time period.

According to yet another embodiment, a body implantable system is configured to implement an atrial arrhythmia monitoring methodology of the present invention. The body implantable system may constitute a bradycardia pacemaker, an atrial only device or a dual chamber defibrillator, for example. The body implantable system includes a lead system having at least an atrial electrode. A detector, coupled to the lead system, senses atrial rhythms.

A first timing circuit detects occurrences of classified atrial fibrillation (AF) rhythms and measures a duration of time (AF time duration) associated with each of the detected atrial fibrillation rhythms. A second timing circuit detects occurrences of classified supraventricular tachycardia (SVT) rhythms other than atrial fibrillation rhythms and measures a duration of time (SVT time duration) associated with each of the detected SVT rhythms. A processor, communicatively coupled to the detector and the timer circuit, produces trend data with respect to a predetermined period of time using the measured AF and SVT time durations.

The processor, according to one embodiment, is disposed within the body implantable system or, in accordance with another embodiment, is disposed within a processing system external to the body implantable system, such as within a programmer. According to a further embodiment, the processor is a distributed processor comprising a first processor disposed within the body implantable system and a second processor disposed within a processing system external to the body implantable system.

The processor may produce trend data by summing the AF time durations to produce a cumulative AF time duration for the predetermined time period, and summing the SVT time durations to produce a cumulative SVT time duration for the predetermined time period. The processor may further compute changes in the cumulative AF time duration as a function of time over the predetermined time period, and compute changes in the cumulative SVT time duration as a function of time over the predetermined time period.

The processor may also produce trend data by computing, using the AF time durations, a percentage (AF percentage) of the predetermined time period during which the classified AF rhythms were detected, and by computing, using the SVT time durations, a percentage (SVT percentage) of the predetermined time period during which the classified SVT rhythms were detected. The processor computes changes in the AF percentage as a function of time over the predetermined time period, and computes changes in the SVT percentage as a function of time over the predetermined time period.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Figure 1:
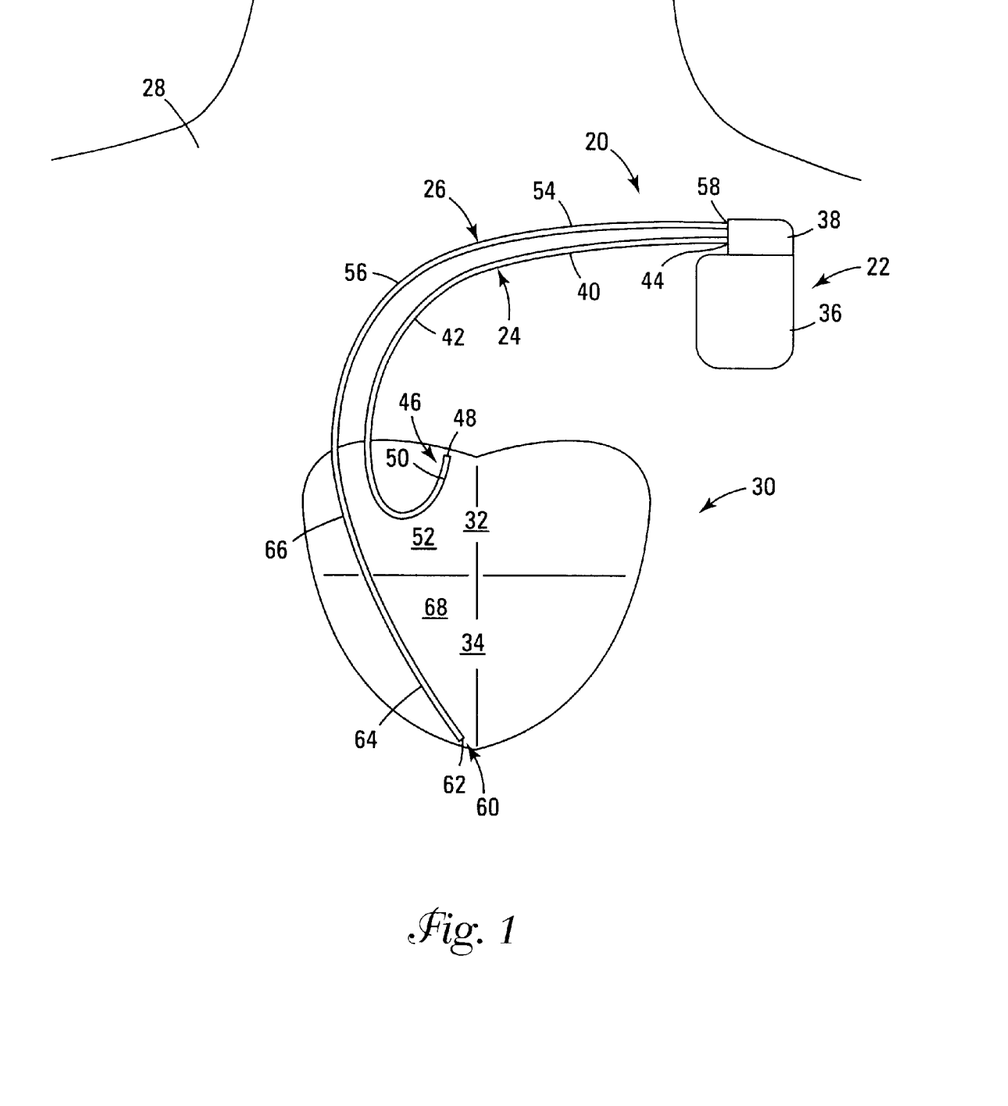
FIG. 1 is a depiction of an implantable medical device with which the atrial arrhythmia monitoring methodologies of the present invention may be practiced.

Referring now to the figures, and more particularly to FIG. 1, there is shown a body implantable system 20 that represents one of several types of systems with which atrial arrhythmia monitoring methodologies of the present invention may be practiced. For example, the implantable pulse generator 22 may be representative of all or part of a pacemaker, defibrillator, cardioverter, cardiac monitor, or re-synchronization device. By way of specific example, the pulse generator 22 may be implemented in a bradycardia pacemaker, an atrial only device or a dual chamber defibrillator. Accordingly, the atrial arrhythmia monitoring methodologies of the present invention may be practiced in a wide variety of implantable medical devices that sense cardiac activity.

The body implantable system 20 is shown to include an implantable pulse generator 22 coupled to an atrial lead 24 and a ventricular lead 26. The system 20 may also include endocardial pacing and cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at a desired site.

The system 20, as shown in FIG. 1, is implanted in a human body 28 with portions of the atrial and ventricular leads 24 and 26 inserted into a heart 30 to detect and analyze electric cardiac signals produced by both the atria 32 and the ventricles 34 of the heart 30. The atrial and ventricular leads 24 and 26 also provide electrical energy to the heart 30 under certain predetermined conditions to treat various types of cardiac arrhythmia, including, for example, atrial and ventricular tachycardias, various types of supraventricular tachyarrhythmias, and atrial and ventricular fibrillation of the heart 30. It is understood that ventricular lead 26 and associated circuitry need not be included in an atrial only pacing generator 22.

As is further shown in FIG. 1, a connector block 38 is mounted on the implantable pulse generator 22. The connector block 38 has two connector ports for coupling the atrial lead 24 and the ventricular lead 26 to the detector 104 and the therapy delivery unit 106 of the implantable pulse generator 22. Additional connector ports can be added to the connector block 38, as in the case of configurations having three or more ports as is known in the art. Alternatively, the connector block 38 can be provided with one connector port for coupling an implantable transvenous lead to the implantable pulse generator 22. It is understood that atrial and ventricular sensing and pacing/defibrillating functions may be accomplished using a single lead system employing atrial and ventricular conductors/electrodes, rather than by use of the dual lead system shown in FIG. 1.

In general, the electrical activity in the heart 30 is sensed, and therapies are delivered to the heart 30, through at least one transvenous pacing/defibrillation lead connected to the implantable pulse generator 22. Unipolar and/or bipolar pacing and sensing electrodes can be used in conjunction with the transvenous pacing/defibrillation lead. In the embodiment shown in FIG. 1, bipolar leads and sensing circuits are utilized for sensing both the atrial 32 and the ventricular 34 activity. Sensing atrial activity includes the determination of atrial P-waves for purposes of determining atrial intervals. Ventricular activity is monitored by sensing for the occurrence of ventricular R-waves for purposes of determining ventricular intervals. Pacing therapies to the atrium 32 or ventricle 34 are delivered to the heart 30 using these same leads.

The system 20 may also employ defibrillation electrodes which are connected to the electrical output connections 112, and serve to deliver cardioversion and defibrillation level electrical pulses to the heart 30 as determined by the programming of controller 100. The housing 36 of the system 20 may be used as an optional defibrillation electrode, where the housing 36 of the implantable pulse generator 22 is electrically connected to a cathode pole of the therapy delivery unit 106. All defibrillation electrical pulses are delivered to the heart with at least two defibrillation electrodes, or through at least one defibrillation electrode and the housing 36 of the implantable pulse generator 22. The system 20 supports a plurality of pacing regimens.

In addition to the lead configuration shown in FIG. 1, the system 20 supports several other lead configurations and types. For example, it is possible to use ventricular epicardial rate sensing, atrial endocardial bipolar pace/sensing, ventricular endocardial bipolar pace/sensing, epicardial patches, and ancillary leads in conjunction with the implantable pulse generator 22.

In the embodiment of system 20 depicted in FIG. 1, the atrial lead 24 has an elongated body 40 having a peripheral surface 42, proximal and distal ends, 44 and 46, a first atrial electrode 48, and a second atrial electrode 50 on the peripheral surface 42. The first atrial electrode 48 and the second atrial electrode 50 receive bipolar electrical cardiac signals from the right atrium chamber 52 of the heart 30, and are attached on the peripheral surface 42 of the elongated body 40.

The first atrial electrode 48 is situated at or adjacent to the distal end 46 of the elongated body 40 and is either a pacing tip electrode or a semi-annular or annular electrode partially or completely encircling the peripheral surface 42 of the elongated body 40. The second electrode 50 is an annular or semi-annular electrode encircling or partially encircling the peripheral surface 42 of the elongated body 40. The second electrode 50 is spaced longitudinally along the peripheral surface 40 from the first atrial electrode 48 and the distal end 46 of the atrial lead 24, such that when the atrial lead 24 is inserted into the right atrial chamber 52 of the heart 30, the first atrial electrode 48 is in physical contact with a portion of a wall of the right atrial chamber 52 of the heart 30 and the second electrode 50 is within the right atrium chamber 52.

Electrical conductors extend longitudinally within the elongated body 40 of the atrial lead 24 from a connection end at the proximal end 44 and make connection to the first and second atrial electrodes 48 and 50. The proximal end 44 of the atrial pacing lead 24 is attached to the connector block 38 of the implantable pulse generator 22. The connector block 38 provides electrical coupling between the contact ends of the electrical conductors of atrial lead 24 with the atrial sense amplifier of the detector 104 and the therapy delivery unit 106, such that the implantable pulse generator 22 receives bipolar signals from, and delivers bipolar pacing to, the right atrium 52 of the heart 30.

The ventricular lead 26 includes an elongated body 54 having a peripheral surface 56, proximal and distal ends, 58 and 60, and a ventricle pacing electrode 62. The ventricular lead 26 also includes a first defibrillation electrode 64 and a second defibrillation electrode 66 situated on the peripheral surface 56 of the elongated body 54. The ventricular pacing electrode 62 and the first defibrillation electrode 64 are adapted to receive electrical cardiac signals from the right ventricle chamber 68 of the heart 30, and are attached on the peripheral surface of the elongated body 54. The second defibrillation electrode 66 is spaced apart and longitudinally on the peripheral surface 56 of the ventricular lead 26. This configuration affords positioning of the ventricular lead 26 in the heart 30 with the ventricular pacing electrode 62 in the apex of the right ventricle 68, the first defibrillation electrode 64 within the right ventricle chamber of the heart, and the second defibrillation electrode 66 within the right atrium chamber 52 or a major vein leading to right atrium.

Electrical leads extend longitudinally within the elongated body 54 of the ventricular lead 26 from a connection end at the proximal end 58 to make connection with the ventricular pacing electrode 62, the first defibrillation electrode 64, and the second defibrillation electrode 66. The proximal end 58 of the ventricular lead 26 is attached to the connector block 38 of the implantable pulse generator 22. The connector block 38 provides for electrical coupling between the contact ends of the electrical conductors of ventricular lead 26 with the ventricular sense amplifier of the detector 104 and the therapy delivery unit 106, such that the implantable pulse generator 22 receives either unipolar or bipolar signals from, and can deliver unipolar or bipolar pacing to, the right ventricle 68 and defibrillation electrical pulses to the ventricles 34 of the heart 30.

The atrial lead 24 and the ventricular lead 26 are releasably attached to, and are separated from, the implantable pulse generator 22 to facilitate insertion of the atrial lead 24 into the heart 30. The proximal end 44 of the atrial lead 24 and the proximal end 58 of the ventricular lead 26 are adapted to seal together with the connector ports of the implantable pulse generator 22 to thereby engage the contact ends of the atrial lead 24 and the ventricular lead 26 with the plurality of electrical connections 110 and the therapy delivery unit 106 of the implantable pulse generator 22. The implantable pulse generator 22 of the system 20 is then positioned subcutaneously within the body 26.

Figure 2:
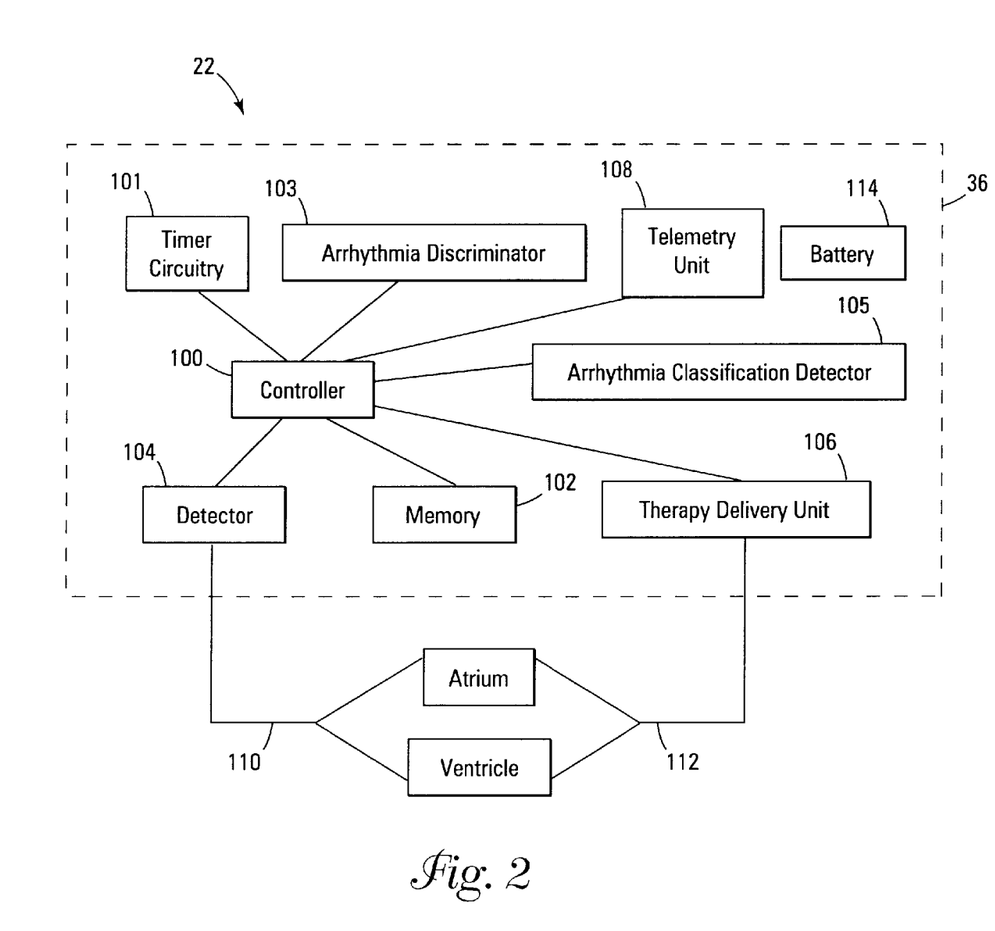
FIG. 2 is a block diagram showing several components housed in the implantable medical device of FIG. 1.

A block diagram of the implantable pulse generator 22 electronics is provided in FIG. 2. The implantable pulse generator 22 includes a housing 36 which contains, among other components, a controller 100 and memory 102, which typically includes read only memory (ROM) and random access memory (RAM). Pulse generator 22 further includes a detector 104, which includes atrial and ventricular sense amplifiers (not shown), a therapy delivery unit 106, and a telemetry unit 108. It is understood that ventricular sense amplifiers, as well as ventricular leads, electrodes, and ancillary electronics and software, need not be provided in an implantable medical device (IMD) that provides for sensing and pacing of only the atria.

The electronic components of the pulse generator 22 are interconnected by way of a bus connection (not shown). Power to the implantable pulse generator 22 is supplied by an electrochemical battery 114 which is contained within the implantable pulse generator housing 36. The implantable pulse generator 22 is interrogated and programmed via bidirectional radio frequency telemetry through cooperative operation between the telemetry unit 108 and an external programmer in a manner known in the art.

The atrial arrhythmia monitoring methodologies implemented by system 20 are embodied in one or more algorithms as firmware within memory 102, and are executed by the controller 100. The detector 104 is also connected to the controller 100, and contains a plurality of electrical connections 110 coupled to the atrial and, if applicable, ventricular sense amplifiers. The outputs of the sense amplifiers are connected to the controller 100, such that atrial and ventricular signals received through the detector 104 are analyzed by the algorithms implemented within the controller 100. The controller 100 is also coupled to the therapy delivery unit 106, which controls the delivery of electrical energy to the heart 30 through a plurality of electrical output connections 112 to affect the sinus rhythm of the heart 30 under certain combinations of atrial 32 and ventricular 34 conditions.

As is further shown in FIG. 2, the pulse generator 22 includes arrhythmia discrimination circuitry 103 which is coupled to the controller 100. The arrhythmia discrimination circuitry 103 may alternatively be coupled to, or integral with, the detector 104. The arrhythmia discrimination circuitry 103 employs one or more discrimination algorithms to classify arrhythmias detected by the detector 104. Various known approaches to discriminating and classifying atrial and, if applicable, ventricular arrhythmias may be employed.

In an embodiment that provides for monitoring atrial arrhythmias, the arrhythmia discrimination circuitry 103 cooperates with the detector 104 to classify two or more types of atrial arrhythmias. Of the various types of arrhythmias that originate in the atria, a number of these atrial arrhythmias can be classified by the arrhythmia discrimination circuitry 103 using known techniques. Although the nomenclature varies within the industry, the various types of arrhythmias that originate in the atria include: atrial fibrillation (paroxsymal, persistent, and permanent); atrial flutter (typical and atypical); sinus arrhythmia; sinus tachycardia; sick sinus syndrome; premature supraventricular contracts or premature atrial contractions (PAC); supraventricular tachyarrhythmia (SVT), including paroxysmal atrial tachycardia (PAT); and Wolff-Parkinson-White Syndrome. Other names given for arrhythmias that originate in the atria include ectopic atrial tachycardia; multifocal atrial tachycardia; AV node re-entry; orthodromic, and atrioventricular re-entry.

The arrhythmia discrimination circuitry 103 can be programmed to discriminate between several of the above-listed atrial arrhythmias and to classify detected atrial arrhythmias into appropriate classification categories. According to one particular embodiment, for example, the arrhythmia discrimination circuitry 103 is programmed to classify detected atrial arrhythmias into two major classes: an atrial fibrillation (AF) class and a supraventricular tachyarrhythmia (SVT) class. It is noted that the term SVT, as understood by some in the art, represents a collection of atrial arrhythmias that includes atrial fibrillation. In other words, AF is often considered to be a species of SVT.

Irrespective of such differences in the vernacular, the arrhythmia discrimination circuitry 103 can, according to this particular embodiment, be programmed to classify two groups of atrial arrhythmias: (1) AF and (2) SVTs other than AF. In another embodiment, the arrhythmia discrimination circuitry 103 can be programmed to classify three groups of atrial arrhythmias: (1) AF; (2) atrial flutter; and (3) SVTs other than AF and atrial flutter. Those skilled in the art will appreciate that the arrhythmia discrimination circuitry 103 can be programmed to classify up to as many atrial arrhythmias as is possible or desired to distinguish, depending on the available discrimination hardware and software of the body implantable device 20, as well as power and memory allocation constraints. Accordingly, the arrhythmia discrimination circuitry 103 classifies atrial arrhythmias into at least an AF class and n number of SVT classes (e.g., $SVT_1$, $SVT_2$, . . . $SVT_n$), noting that n can equal 1 in certain configurations.

The pace generator 22 depicted in FIG. 2 also includes an arrhythmia classification detector 105, which is shown coupled to the controller 100. The arrhythmia classification detector 105 may alternatively be coupled to, or integral with, the arrhythmia discrimination circuitry 103 or the detector 104. The arrhythmia classification detector 105 operates to detect when a particular atrial arrhythmia has been classified by the arrhythmia discrimination circuitry 103. For example, the arrhythmia discrimination circuitry 103 may process atrial events at a time $T_1$ and determine that the patient is experiencing an AF rhythm. At a time $T_2$, the arrhythmia discrimination circuitry 103 may process atrial events and determine that the patient is experiencing an SVT rhythm.

As such, the arrhythmia discrimination circuitry 103 performs an arrhythmia discrimination function. The arrhythmia classification detector 105, in contrast, detects when the arrhythmia discrimination circuitry 103 has identified a detected arrhythmia as belonging to a particular classification category. In response to detecting a classification decision made by the arrhythmia discrimination circuitry 103, the arrhythmia classification detector 105 activates appropriate timing circuitry to implement the atrial arrhythmia monitoring methodologies of the present invention.

The timer circuitry 101, shown coupled to the controller 100 in FIG. 2, includes several timing circuits. In addition to timing circuits, the timer circuitry 101 may also include counting circuits, depending on the functionality of a given implementation. In general, at least one timing circuit is allocated for each atrial arrhythmia to be monitored. In a configuration that includes counting circuits, at least one timing circuit and at least one counting circuit is allocated for each atrial arrhythmia to be monitored.

Figure 3:
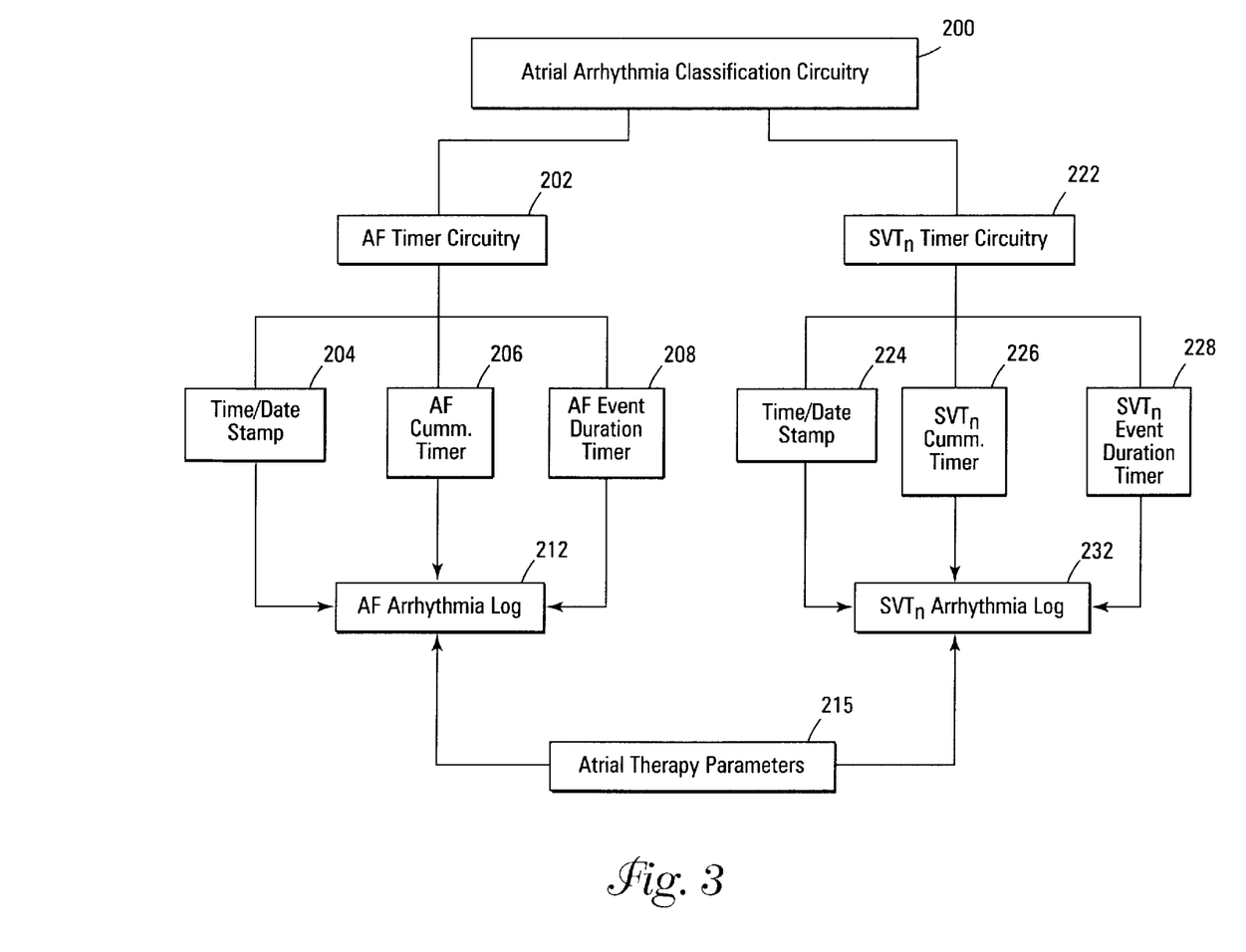
FIG. 3 is a block diagram showing several components associated with atrial fibrillation (AF) and supraventricular tachyarrhythmia (SVT) monitoring circuitry in accordance with an embodiment of the present invention.

Referring now to FIG. 3, there is shown a block diagram of several components of an atrial arrhythmia monitoring system implemented in accordance with an embodiment of the present invention. The system depicted in FIG. 3 includes atrial arrhythmia classification circuitry 200, which typically includes the arrhythmia discrimination circuitry 103 and the arrhythmia classification detector 105 shown in FIG. 2. The atrial arrhythmia classification circuitry 200 classifies atrial arrhythmias into n number of preprogrammed categories or classes. In the embodiment shown in FIG. 3, the atrial arrhythmia classification circuitry 200 classifies atrial arrhythmias into an AF class and one or more SVT classes.

As is further depicted in FIG. 3, AF timer circuitry 202 is shown to include several elements, including an AF cumulative timer 206, an AF rhythm duration timer 208, and a time/date stamp circuit 204. Each of these AF elements 204, 206, and 208 is coupled to an AF arrhythmia log 212. The AF arrhythmia log 212 may also receive and store atrial therapy parameters 215, such as time and date of a delivered atrial therapy, voltage, duration, and energy expended data, for example.

Also shown coupled to the atrial arrhythmTia classification circuitry 200 is SVT timer circuitry 222. SVT timer circuitry 222 is shown to include several elements, including an SVT cumulative timer 226, an SVT rhythm duration timer 228, and a time/date stamp circuit 224. Each of these SVT elements 224, 226, and 228 is coupled to an SVT arrhythmia log 232. The SVT arrhythmia log 232 may also receive and store atrial therapy parameters 215.

It is noted that SVT timer circuitry as described above may be allocated for each type of SVT to be monitored. It is further noted that the functions performed by several of the AF and SVT elements depicted in FIG. 3 can, in certain implementations, be performed by common or shared elements, rather than by the distinct elements depicted for illustrative purposes in FIG. 3. Further, it is understood that the atrial arrhythmia classification circuitry, timer circuitry, and other date/time elements described herein can be implemented in hardware, software, or a combination of hardware and software.

In response to classifying a detected atrial arrhythmia, the atrial arrhythmia classification circuitry 200 invokes the timer circuitry associated with the classified atrial arrhythmia. For example, and as shown in FIG. 3, AF timer circuitry 202 is invoked in response to the atrial arrhythmia classification circuitry 200 having classified an atrial arrhythmia as atrial fibrillation. The AF rhythm duration timer 208 is initiated, as is the AF cumulative timer 206. The time/date stamp circuit 204 generates time and date data to associate the current time and date with the initiation of the AF rhythm duration timer 208.

When the atrial arrhythmia classification circuitry 200 detects that the atrial fibrillation has ceased, either naturally or via delivery of atrial therapy, the AF rhythm duration and cumulative timers 206, 208 are stopped. The time/date stamp circuit 204 may generate the current time and date designating ceasing of the atrial fibrillation rhythm. The duration of the atrial fibrillation rhythm may be computed using the time recorded by AF rhythm duration timer 208. Alternatively, the duration of the atrial fibrillation rhythm may be computed using the difference between the ending and beginning time/date stamp data. The AF rhythm duration timer 208 is reset, typically to zero.

It will be appreciated that the timing functions described in connection with the AF timer circuitry 202 are similarly applicable for the SVT timer circuitry 222 in response to detection of a particular SVT rhythm by the atrial arrhythmia classification circuitry 200. The data generated by the elements of the AF and SVT timer circuitry 202, 222 are stored in the AF and SVT arrhythmia logs 212, 232, respectively. These data are processed by an on-board processor, an external processor (i.e., a processor of a programmer), or a combination of on-board and external processors to generate various types of diagnostic output data, including various trend data.

Figure 4:
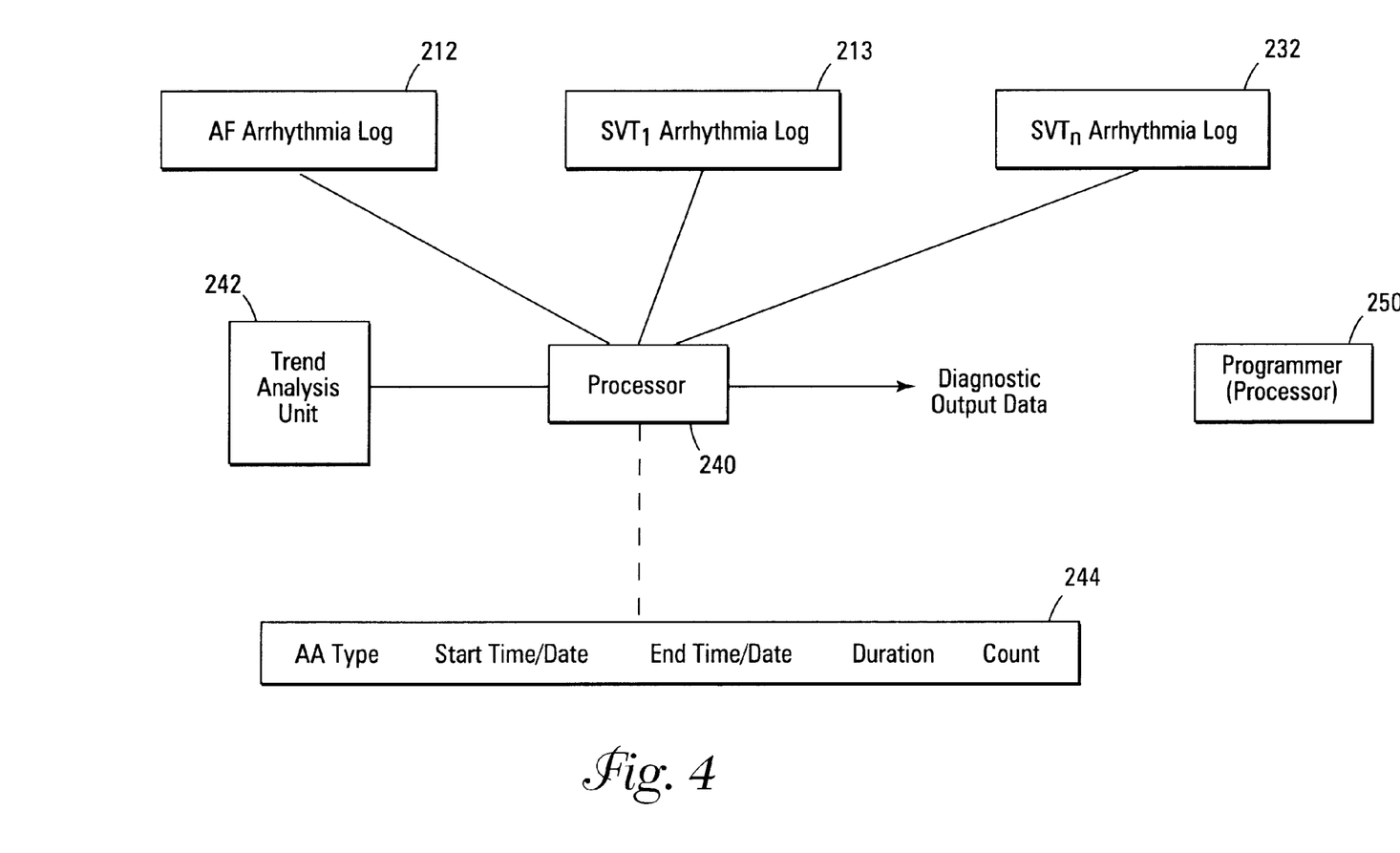
FIG. 4 is a block diagram showing various components associated with atrial fibrillation (AF) and supraventricular tachyarrhythmia (SVT) monitoring and trend analysis circuitry in accordance with an embodiment of the present invention.

FIG. 4 is a block diagram depicting several components that process atrial arrhythmia timing data. As was discussed previously, the data generated by the elements of the AF and SVT timer circuitry are stored in arrhythmia logs associated with each of the atrial arrhythmia types discriminated by the body implantable device 20. In the depiction of FIG. 4, for example, AF timing data is stored in an AF arrhythmia log 212. The timing data associated with the various types of SVTs are stored in respective SVT arrhythmia logs 213 through 232 (i.e., n arrhythmia logs for n number of SVTs, e.g., $SVT_1$ through $SVT_n$). It is understood that the distinct arrhythmia logs 212, 213, 232 shown in FIG. 4 may instead be implemented as a single atrial arrhythmia log. Moreover, it is understood that the arrhythmia logs 212, 213, 232 may be supported in memory 102 of the body implantable system 20, in a memory of an external programmer 250, or in memories of both the body implantable system 20 and the external programmer 250. It is further understood that the external processor 250 may be a processor of a relay station typically provided at the bed side of a patient.

A processor 240 is coupled to the arrhythmia logs 212, 213, 232 and to a trend analysis unit 242. In one embodiment, the processor 240 is incorporated within the body implantable system 20. For example, the processor 240 may be incorporated into, or is representative of, the controller 100 shown in FIG. 2.

In another embodiment, the processor that processes atrial arrhythmia timing data is a distributed processor, such that the atrial arrhythmia timing data is managed by at least two cooperatively operating processors. In FIG. 4, for example, processor 240, provided within the body implantable system 20, and a processor 250, which is situated external to the body implantable system 20, operate cooperatively to manage and process the atrial arrhythmia timing data. The processor 250 is typically a processor of an external programmer. In this embodiment, a trend analysis unit 242 may be coupled to one or both of the processors 240, 250.

In a further embodiment, processor 250 of the external programmer may perform data processing operations on the atrial arrhythmia timing data. In this case, the trend analysis unit 242 can be coupled to the external processor 250.

The processor 240 and/or 250 cooperates with the trend analysis unit 242 to produce various types of diagnostic output data. Data set 244 shown in FIG. 4, for example, represents a non-exhaustive set of input data which the processor 240/250 manages when producing diagnostic output data.

Figure 8:
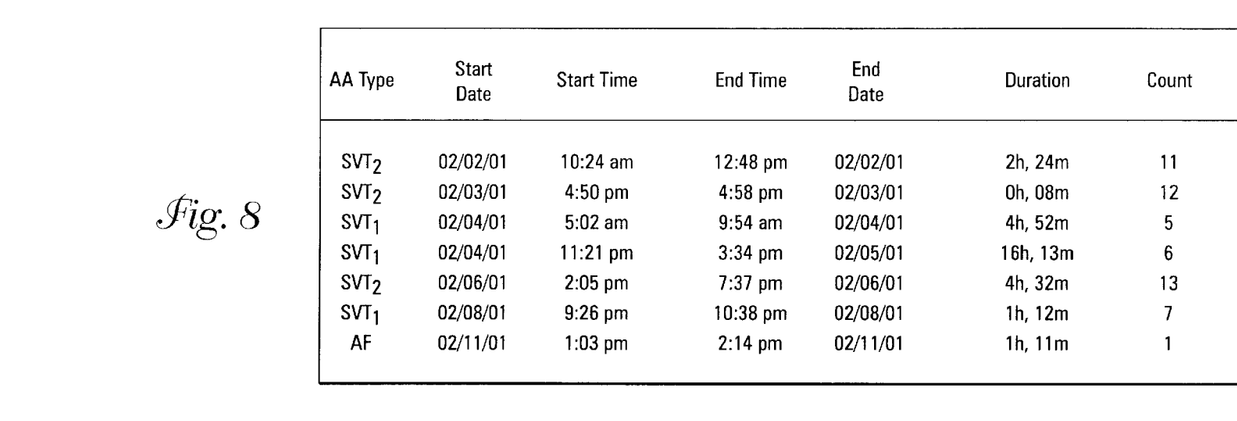
FIG. 8 is an illustrative set of atrial arrhythmia data acquired over several days of atrial monitoring in accordance with an embodiment of the present invention.

FIG. 8, by way of further example, is an illustrative set of atrial arrhythmia data acquired through atrial monitoring of a patient over several days. As can be seen in FIG. 8, data associated with each classified atrial arrhythmia is recorded in one or more arrhythmia logs, a single log being depicted in FIG. 8. Data representative of the type of atrial arrhythmia (M) detected, starting and ending times and dates, duration, and count are recorded.

Figure 9:
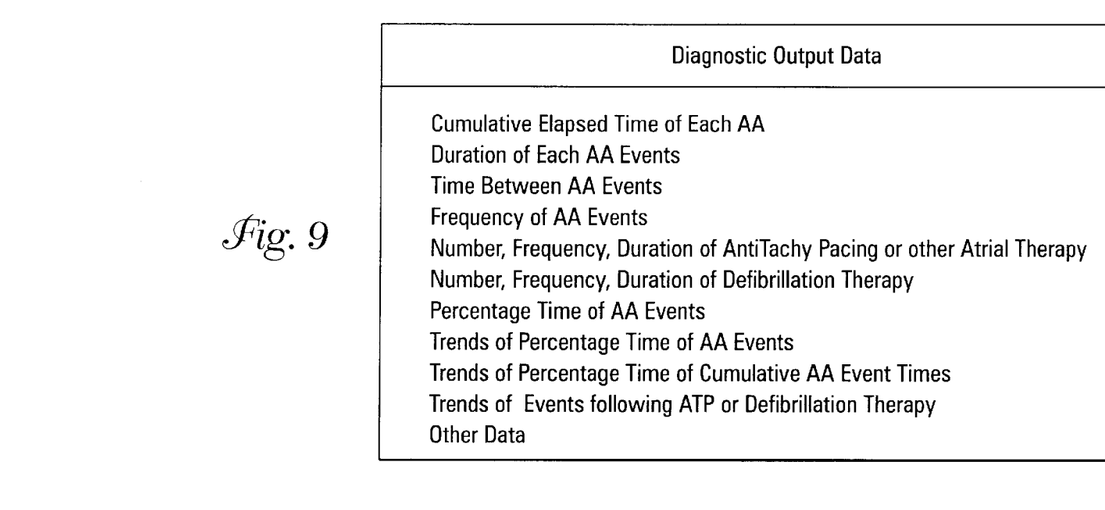
FIG. 9 illustrates a non-exhaustive set of diagnostic output data producible from the recorded atrial arrhythmia data shown in FIG. 8.

The processor 240/250, typically in cooperation with a trend analysis unit 242, produces various types of diagnostic output data using the recorded data shown in FIG. 8. FIG. 9 illustrates a non-exhaustive set of diagnostic output data producible from the recorded data shown in FIG. 8.

For example, the physician may wish to review any atrial arrhythmic activity for a given patient over a predetermined period of time. The physician, using an external programmer 250 or other computer system, may select the time parameters of interest, such as by inputting a beginning date/time and an ending date/time to define a time span of interest, such as a time span between patient evaluation visits with the physician. The physician may also select only a beginning time/date or only an ending time/date. Alternatively, no data/time input need be made by the physician, in which case all available atrial arrhythmia data is processed for such a query.

It is understood that several preprogrammed selectable time spans, such as one or more days (e.g., the last 48 hours), one or more months, or one or more years may be made available for ease of use. It is further understood that atrial arrhythmia data may be accumulated during the service life of each implantable medical device implanted into a patient over the patient's lifetime.

The processor 240/250 can generate various types of output data, including data representative of the raw data stored in the arrhythmia logs and processed diagnostic output data, which may include trend data. As shown in FIG. 9, for example, the processor 240/250 can generate cumulative elapsed time data for all or selected atrial arryhthmias that occurred over a predetermined period of time. The duration of each atrial arrhythmia rhythm, the time between atrial arrhythmia rhythms, and the frequency of each atrial arrhythmia rhythm over a predetermined period of time may also be computed by the processor 240/250. Data concerning the number, frequency, and/or duration of cardioversion, antitachycardia pacing, or defibrillation therapies delivered over a predetermined period of time may also be used, together with other atrial arrhythmia data, by the processor 240/250 to provide for the generation of enhanced diagnostic data.

Various trend data can be generated by the processor 240/250 operating cooperatively with the trend analysis unit 242. The trend analysis unit 242 represents a collection of data processing algorithms stored in memory that operate on the atrial arrhythmia data to produce the various types of trend data and other diagnostic output data. For example, the percentage of time for which each or a selected atrial arrhythmia occurred during a predetermined period of time can be generated. Trends associated with each or a selected atrial arrhythmia that occurred during a predetermined period of time can also be generated. For example, trends in the duration or percentage of time of each or a selected atrial arrhythmia with respect to a predetermined period of time may be computed.

Changes in the duration or percentage of time during which a patient experienced atrial fibrillation over a preprogrammed time period may be determined. This trend data may show reductions or increases in AF rhythms over time, such as before and after a time at which AF therapy was delivered. Trends in the data occurring before and after cardioversion, antitachycardia pacing or other atrial therapy may likewise be computed.

It is understood that other types of output data may be developed using the atrial arrhythmia data. Various known statistical modeling and processing techniques can be applied to the atrial arrhythmia data to produce desired diagnostic output data. This data may be used by the physician when evaluating a patient's condition and when developing or administering a treatment program for the patient.

Figure 5:
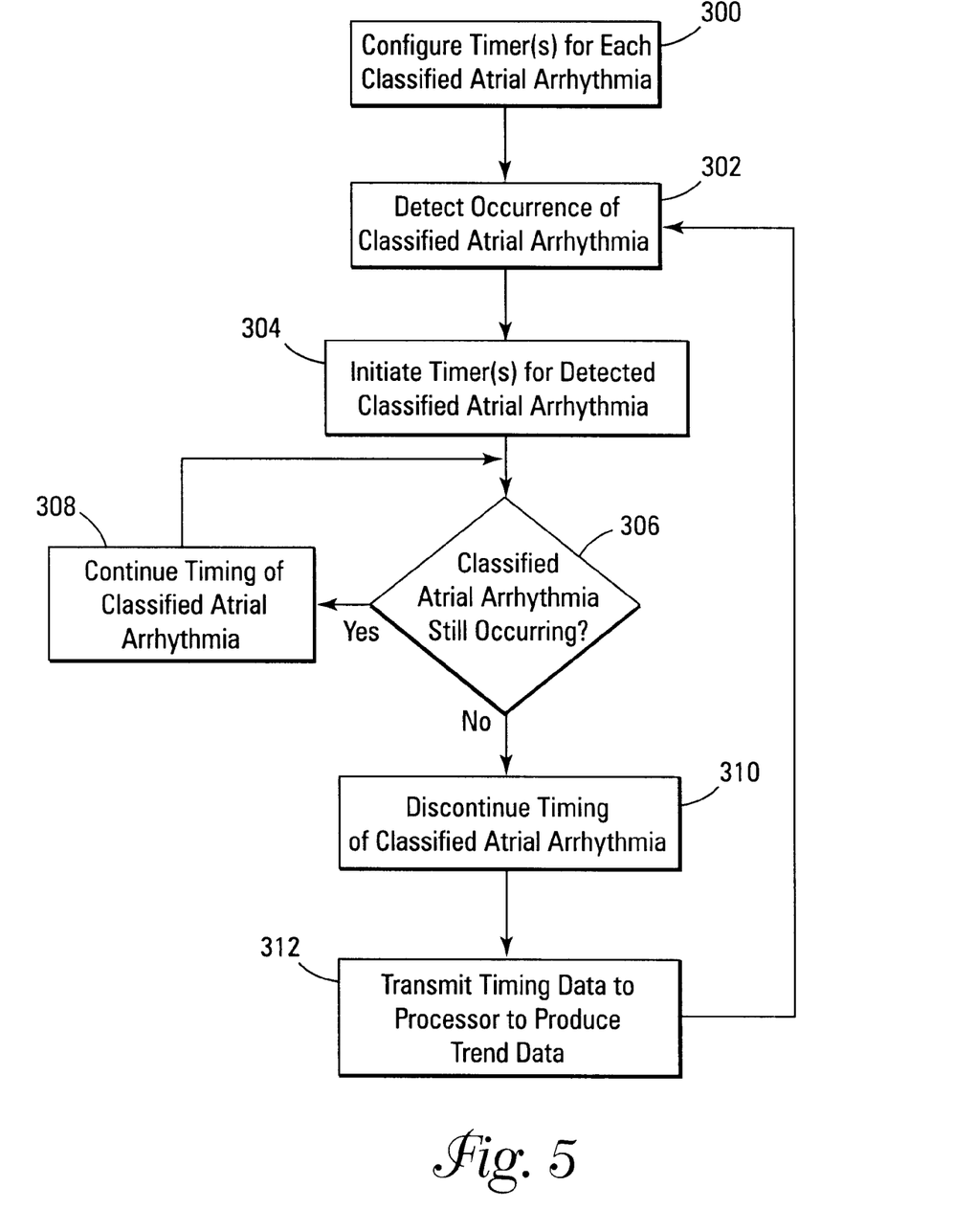
FIG. 5 is a flow chart depicting various processes of an atrial arrhythmia monitoring methodology in accordance with an embodiment of the present invention.

Turning now to FIG. 5, there is illustrated various processes for implementing an atrial arrhythmia monitoring methodology in accordance with an embodiment of the present invention. According to this embodiment, one or more timers and, if applicable, counters are configured 300 for each classified atrial arrhythmia to be monitored. Such configuration operations may include, for example, verifying the accuracy of a time/data stamp, if used, resetting certain timers and/or counters, and verifying the sufficiency of memory to support the timers.

Upon detection 302 of a classified atrial arrhythmia, the timer(s) associated with the detected classified atrial arrhythmia are initiated 304. Timer operations continue 306, 308 until the classified atrial arrhythmia ceases. Timing operations are discontinued 310, and certain timers may be reset. The timing data is transmitted 312 to the processor, from which diagnostic and trend data can be produced. The trend data may be formatted in one or more formats, such as in a time bin format or a log format, for example.

Figure 6:
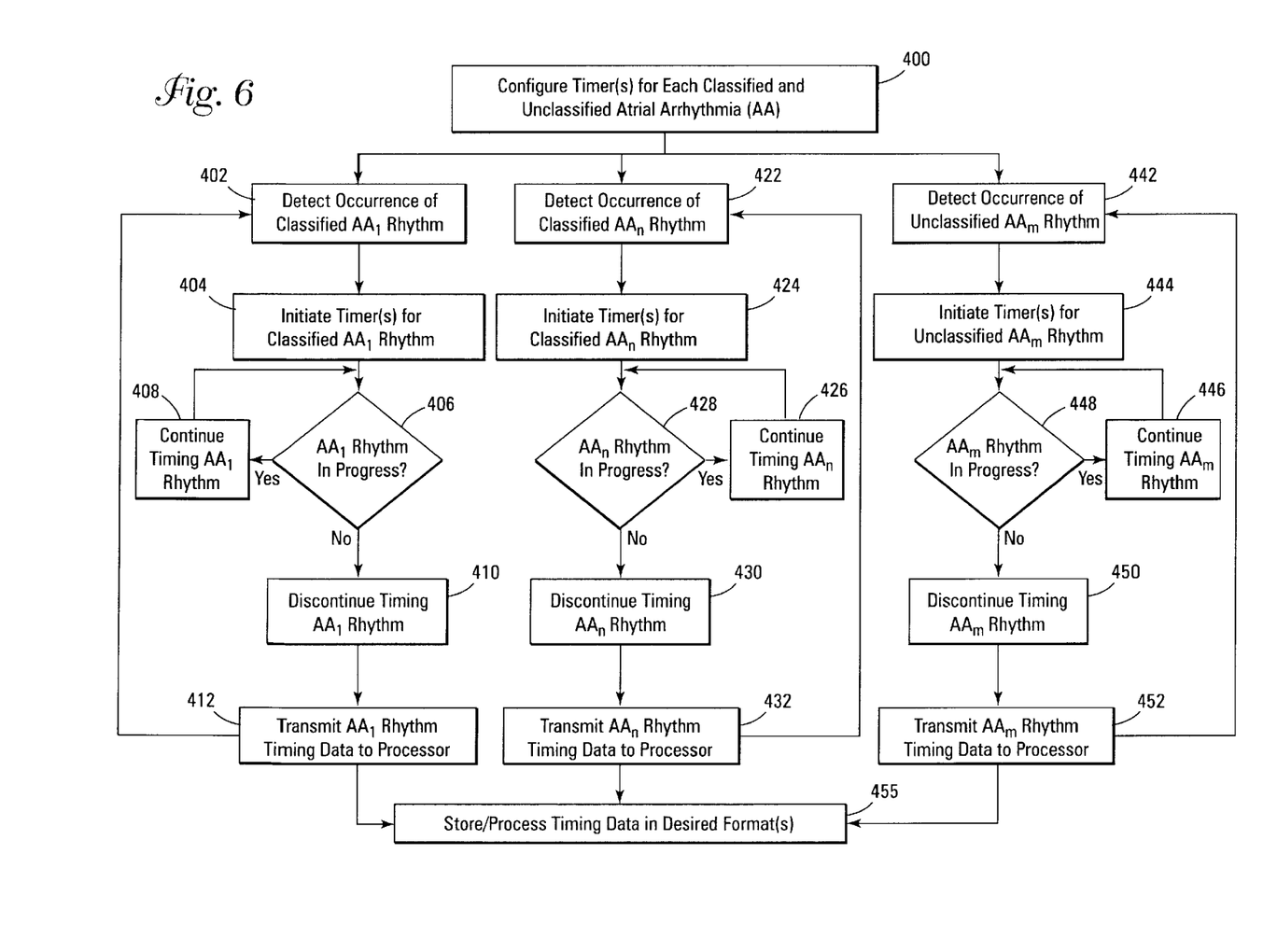
FIG. 6 is a flow chart depicting various processes of an atrial arrhythmia monitoring methodology for monitoring several classified and unclassified atrial arrhythmias in accordance with an embodiment of the present invention.

FIG. 6 illustrates various processes for implementing an atrial arrhythmia monitoring methodology in accordance with another embodiment of the present invention. In this embodiment, a number n of timers are configured 400 for each classified atrial arrhythmia. In addition, one or more timers are configured for a corresponding one or more unclassified atrial arrhythmias. In this context, an unclassified atrial arrhythmia represents a detected arrhythmia originating in the atria that does not satisfy the criteria established for the various classified atrial arrhythmias. One or more timers and, if applicable, counters can be configured for purposes of monitoring such unclassified atrial arrhythmias.

In the illustrative embodiment of FIG. 6, detection 402, 422, 442 of classified and unclassified atrial arrhythmias occurs concurrently, as is the case in other embodiments. Upon detection of a given classified or unclassified atrial arrhythmia, the associated timer circuitry is initiated 404, 424, 444. Timing operations continue 406, 408, 428, 426, 448, 446 until the detected atrial arrhythmia ceases, at which time the associated timing operations are discontinued 410, 430, 450. The acquired timing data are transmitted 412, 432, 452 to the processor, from which diagnostic and trend data can be produced.

The timing data can be stored and/or processed 455 in a variety of formats. For example, the timing data may be formatted in accordance with a time bin format and/or a log format. FIGS. 8 and 9 illustrate arrhythmia timing data formatted and processed using a log format, as will be discussed in greater detail hereinbelow.

Figure 10:
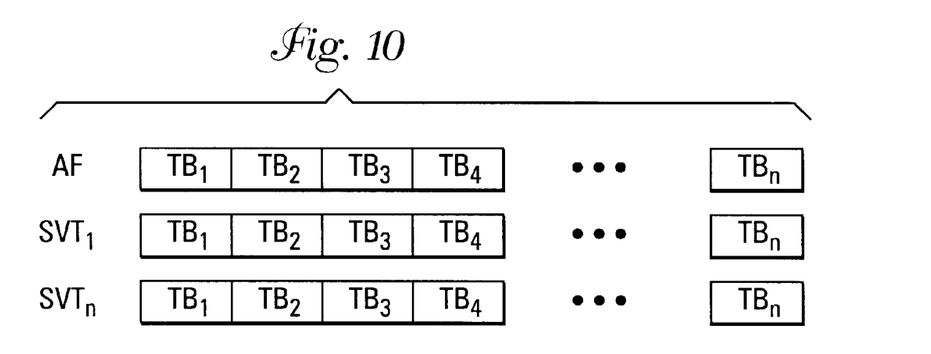
FIGS. 10 and 11 illustrate formatting of atrial arrhythmia data using a time bin format, in contrast to a log format shown in FIGS. 8 and 9.
Figure 11:
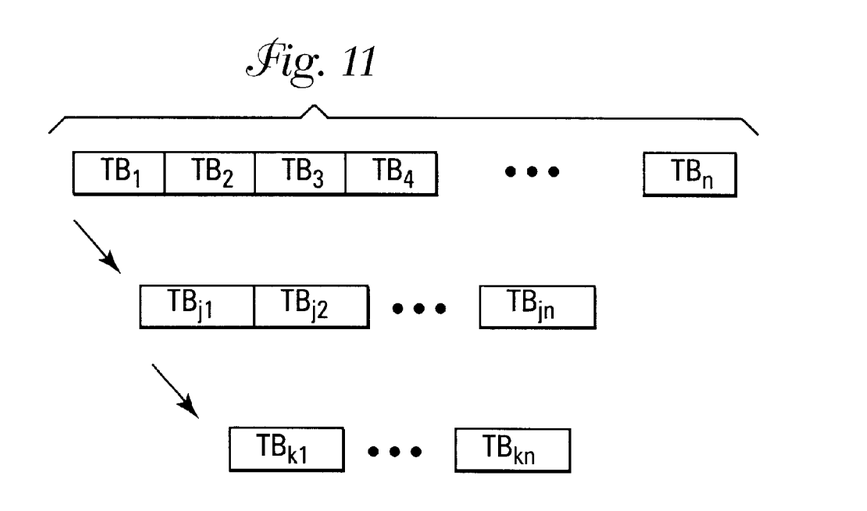

FIGS. 10 and 11 illustrate arrhythmia timing data formatted and processed using a time bin format. According to this format, trend data is developed from arrhythmia timing data formatted in terms of slots or bins of time. FIG. 10 depicts a series of time bins, $TB_1$ through $TB_n$, associated with each type of atrial rhythm to be monitored (e.g., AF, $SVT_1$, $SVT_n$). Each of the time bins represents a duration of time that can range between several seconds and several minutes. For example, each of the time bins, $TB_1$ through $TB_n$, represents a 30 second time duration or a minute time duration.

As atrial rhythm data is acquired, the data is partitioned such that each partitioned segment of atrial rhythm data is associated with a given time bin. Upon detection, each type of atrial rhythm to be monitored is associated with a given time bin. A given time bin may be associated with a single atrial rhythm or several atrial rhythms, depending on the duration of the time bin and the nature of atrial activity occurring within the duration of the time bin. In one embodiment, two time bins are employed, namely, an AF time bin and an SVT time bin. in other embodiments, more than two time bins may be employed, as is indicated in the depiction of FIG. 10.

As can be seen in FIG. 11, a hierarchy of time bins may be employed to provide for multiple levels of data granularity. In FIG. 11, three levels of data granularity are depicted. A first level is defined by time bins $TB_1$ through $TB_n$, where each of these time bins represents a relatively short duration of time (e.g., 30 seconds or a minute). This first level provides the highest level of atrial rhythm data granularity.

A second level is defined by time bins $TB_{j1}$ through $TB_{jn}$, where each of these time bins represents a duration of time longer than those associated with the first level (e.g., 20 minutes or 1 hour). A third level is defined by time bins $TB_{k1}$ through $TB_{kn}$, where each of these time bins represents a duration of time longer than those associated with the second level (e.g., 12 hours or 1 day). The number of data granularity levels and the duration of the time bins associated with each level may be programmed or selected as desired. The levels and time bin durations may be adjusted as needed.

Formatting the atrial rhythm data in terms of time bins facilitates efficient trend analyses. For example, a physician may wish to know the duration of each atrial arrhythmia (e.g., AF and SVT) detected over the past three months or the percentage of total time associated with the occurrence of each atrial arrhythmia over the past six weeks. The physician may also wish to know the breakdown of all atrial arrhythmias that were detected for a given time period. This breakdown may be expressed in terms of time duration or percentage. Using a time bin format provides for efficient processing of atrial rhythm data.

By way of example, an analysis may reveal that over the past four months, the patient experienced an AF rhythm 2 percent of the time and an SVT rhythm 6 percent of the time. By way of further example, the analysis may reveal that of all atrial arrhythmias detected over the past 12 months, 21 percent were AF rhythms, 75 percent were SVT rhythms, and the remaining 4 percent were unclassified atrial arrhythmias. Such trend data is produced in an efficient manner using a time bin format for storing and processing atrial rhythm data.

For purposes of conserving IMD memory space, the more detailed levels of atrial rhythm data may be discarded after being processed and after the results of such processing have been stored at a higher level of data granularity. It may be desired, however, to retain the more detailed atrial rhythm data during a time in which an atrial episode has been declared. This detailed atrial rhythm data can be attached to other episode data and transmitted to an external programmer or other processor for further evaluation.

Figure 7:
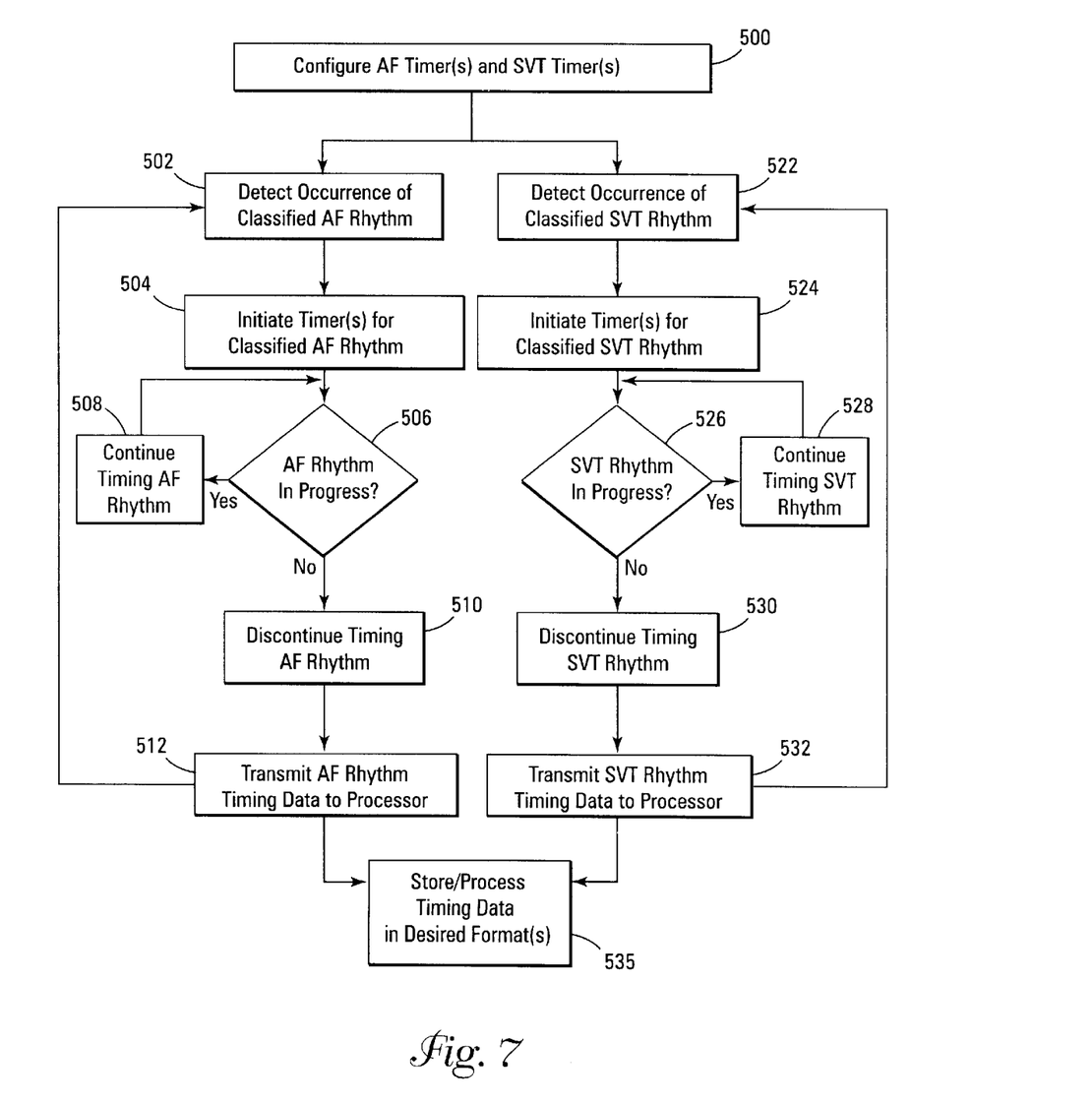
FIG. 7 is a flow chart depicting several processes of an AF and SVT monitoring methodology in accordance with an embodiment of the present invention.

FIG. 7 illustrates one embodiment for analyzing occurrences of two atrial arrhythmias of particular interest. According to this embodiment, atrial fibrillation and SVTs other than AF, such as atrial flutter, are monitored with greater specificity than has heretofore been possible using traditional monitoring approaches. The atrial arrhythmia monitoring methodology according to the present invention provides the physician with detailed and accurate diagnostic data needed to determine optimal medical or device therapy decisions for a given patient.

According to the embodiment shown in FIG. 7, AF and SVT (e.g., atrial flutter) timers are configured 500. Upon detection 502, 522 of a classified AF or SVT rhythm, the associated AF or SVT timer circuitry is initiated 504, 524. Timing operations continue 506, 508, 526, 528 until the detected AF or SVT rhythm ceases, at which time the associated timing operations are discontinued 510, 530. The acquired AF and SVT timing data are transmitted 512, 532 to the processor, from which AF and SVT diagnostic and trend data can be produced.

It will, of course, be understood that various modifications and additions can be made to the various embodiments discussed hereinabove without departing from the scope of the present invention. For example, those skilled in the art will appreciate that the disclosed systems and methods may be employed for analyzing occurrences of classified ventricular arrhythmias, exclusive of, or in addition to, analyzing occurrences of classified atrial arrhythmias. Also, it will be appreciated that atrial episodes may be used as the basis of atrial data collection and monitoring, rather than simply using atrial rhythms.

According to one alternative approach, the arrhythmia discriminator 103 shown in FIG. 2, for example, is programmed to discriminate ventricular arrhythmias using known ventricular arrhythmia discrimination techniques. The arrhythmia classification detector 105 is programmed to detect classified and unclassified ventricular arrhythmias. The timer circuitry shown in FIGS. 2 and 3 is responsive to detect classified and unclassified ventricular arrhythmias in a manner similar to that previously described with respect to detected classified and unclassified atrial arrhythmias. The trend data produced by the controller or processor of FIGS. 2 and 4 is ventricular diagnostic and trend data of a type similar to that produced using atrial arrhythmia data.

Accordingly, the scope of the present invention should not be limited by the particular embodiments described above, but should be defined only by the claims set forth below and equivalents thereof.

What is claimed is:

1. A method of analyzing occurrences of classified atrial arrhythmias, comprising:
    detecting occurrences of classified atrial fibrillation (AF) rhythms;
    detecting occurrences of classified supraventricular tachycardia (SVT) rhythms other than atrial fibrillation rhythms;
    measuring a duration of time (AF time duration) associated with each of the detected atrial fibrillation rhythms;
    measuring a duration of time (SVT time duration) associated with each of the detected SVT rhythms; and
    producing trend data with respect to a predetermined period of time using the measured AF and SVT time durations.

2. The method of claim 1, wherein producing the trend data comprises:
   summing the AF time durations to produce a cumulative AF time duration for the predetermined time period; and
   summing the SVT time durations to produce a cumulative SVT time duration for the predetermined time period.

3. The method of claim 2, wherein producing the trend data further comprises:
   computing changes in the cumulative AF time duration as a function of time over the predetermined time period; and
   computing changes in the cumulative SVT time duration as a function of time over the predetermined time period.

4. The method of claim 1, wherein producing the trend data comprises:
   computing, using the AF time durations, a percentage (AF percentage) of the predetermined time period during which the classified AF rhythms were detected; and
   computing, using the SVT time durations, a percentage (SVT percentage) of the predetermined time period during which the classified SVT rhythms were detected.

5. The method of claim 4, further comprising
   computing changes in the AF percentage as a function of time over the predetermined time period; and
   computing changes in the SVT percentage as a function of time over the predetermined time period.

6. The method of claim 1, wherein the predetermined time period comprises a selectively programmable period of time.

7. The method of claim 1, wherein the predetermined time period comprises a 24 hour time period, a time period based on months or a time period based on years.

8. The method of claim 1, wherein the predetermined time period comprises a time period between patient analyses.

9. The method of claim 1, wherein the predetermined time period comprises a time period defined by a life time of a patient.

10. The method of claim 1, wherein the classified SVT rhythms comprise atrial flutter.

11. The method of claim 1, wherein the respective detecting, measuring, and producing processes are performed for one or more unclassified atrial arrhythmias.

12. A body implantable system, comprising:
   a lead system comprising an atrial electrode;
   a detector, coupled to the lead system, that senses atrial rhythms;
   a first timing circuit that detects occurrences of classified atrial fibrillation (AF) rhythms and measures a duration of time (AF time duration) associated with each of the detected atrial fibrillation rhythms;
   a second timing circuit that detects occurrences of classified supraventricular tachycardia (SVT) rhythms other than atrial fibrillation rhythms and measures a duration of time (SVT time duration) associated with each of the detected SVT rhythms; and
   a processor communicatively coupled to the detector and the timer circuit, the processor producing trend data with respect to a predetermined period of time using the measured AF and SVT time durations.

13. The system of claim 12, wherein the processor is disposed within the body implantable system or within a processing system external to the body implantable system.

14. The system of claim 12, wherein the processor comprises a distributed processor, the distributed processor comprising a first processor disposed within the body implantable system and a second processor disposed within a processing system external to the body implantable system.

15. The system of claim 12, wherein the processor formats the measured AF and SVT time durations using a log format or a time bin format.

16. The system of claim 12, the processor produces the trend data by summing the AF time durations to produce a cumulative AF time duration for the predetermined time period, and summing the SVT time durations to produce a cumulative SVT time duration for the predetermined time period.

17. The system of claim 16, wherein the processor produces the trend data by computing changes in the cumulative AF time duration as a function of time over the predetermined time period, and by computing changes in the cumulative SVT time duration as a function of time over the predetermined time period.

18. The system of claim 12, wherein the processor produces the trend data by computing, using the AF time durations, a percentage (AF percentage) of the predetermined time period during which the classified AF rhythms were detected, and by computing, using the SVT time durations, a percentage (SVT percentage) of the predetermined time period during which the classified SVT rhythms were detected.

19. The system of claim 18, wherein the processor computes changes in the AF percentage as a function of time over the predetermined time period, and computes changes in the SVT percentage as a function of time over the predetermined time period.

20. The system of claim 12, wherein the predetermined time period comprises a selectively programmable period of time.

21. The system of claim 12, wherein the predetermined time period comprises a 24 hour time period, a monthly time period or a yearly time period.

22. The system of claim 12, wherein the predetermined time period comprises a time period between patient analyses or a time period defined by a life time of a patient.

23. The system of claim 12, wherein the classified SVT rhythms comprise atrial flutter.

24. A method of analyzing occurrences of atrial arrhythmias, comprising:
   detecting occurrences of each of a plurality of classified atrial arrhythmia rhythms;
   measuring a duration of time associated with each of the detected atrial arrhythmia rhythms; and
   producing trend data with respect to a predetermined period of time using all or selected ones of the measured time durations.

25. The method of claim 24, wherein producing the trend data comprises summing each of the time durations to produce a cumulative time duration associated with each of the classified atrial arrhythmia rhythms over the predetermined time period.

26. The method of claim 25, wherein producing the trend data further comprises computing changes in the respective cumulative time durations as a function of time over the predetermined time period.

27. The method of claim 24, wherein producing the trend data comprises computing, using each of the time durations, a percentage of the predetermined time period during which each of the classified atrial arrhythmia rhythms was detected.

28. The method of claim 27, further comprising computing changes in the respective percentages as a function of time over the predetermined time period.

29. The method of claim 24, wherein the predetermined time period comprises a selectively programmable period of time.

30. The method of claim 24, wherein the predetermined time period comprises a 24 hour time period, a time period based on months or a time period based on years.

31. The method of claim 24, wherein the predetermined time period comprises a time period between patient analyses.

32. The method of claim 24, wherein the predetermined time period comprises a time period defined by a life time of a patient.

33. The method of claim 24, wherein the classified atrial arrhythmias comprise at least atrial fibrillation and atrial flutter.

34. The method of claim 24, wherein the detecting, measuring, and producing processes are performed for one or more unclassified atrial arrhythmias.

* * * * *